(12) United States Patent
Yilmaz et al.

(10) Patent No.: US 8,252,876 B2
(45) Date of Patent: Aug. 28, 2012

(54) IMPRINTED POLYMERS

(75) Inventors: Ecevit Yilmaz, Bjärred (SE); Henrik Björk, Stenstorp (SE); Johan Billing, Lund (SE); Anthony Rees, Furulund (SE)

(73) Assignee: Biotage AB (SE)

( * ) Notice: Subject to any disclaimer, the term of this patent is extended or adjusted under 35 U.S.C. 154(b) by 0 days.

(21) Appl. No.: 12/527,659

(22) PCT Filed: Feb. 13, 2008

(86) PCT No.: PCT/EP2008/051729
§ 371 (c)(1),
(2), (4) Date: Nov. 24, 2009

(87) PCT Pub. No.: WO2008/107271
PCT Pub. Date: Sep. 12, 2008

(65) Prior Publication Data
US 2010/0113724 A1  May 6, 2010

(30) Foreign Application Priority Data
Mar. 5, 2007 (SE) ..................... 0700546

(51) Int. Cl.
*C08F 230/06* (2006.01)
(52) U.S. Cl. .......... 526/239; 526/317.1; 526/219.6; 435/7.1; 435/287.2
(58) Field of Classification Search .......... 526/314, 526/239, 219.6, 317.1; 435/6, 7.1, 287.2
See application file for complete search history.

(56) References Cited

U.S. PATENT DOCUMENTS

| 5,994,110 | A |  | 11/1999 | Mosbach et al. |
| 2003/0186330 | A1 |  | 10/2003 | Sode |
| 2004/0063159 | A1 | * | 4/2004 | Mosbach et al. ............... 435/7.1 |
| 2004/0157209 | A1 | * | 8/2004 | Yilmaz et al. ..................... 435/5 |

FOREIGN PATENT DOCUMENTS

| EP | 0982591 A2 | 3/2000 |
| JP | 59223706 A | 12/1984 |
| WO | WO-00/10007 A2 | 2/2000 |
| WO | WO-01/90228 A1 | 11/2001 |
| WO | WO-2006/041370 A1 | 4/2006 |
| WO | WO-2007/117174 A1 | 10/2007 |

OTHER PUBLICATIONS

Whitcombe et al., "A new method for the introduction of recognition site functionality into polymers prepared by molecular imprinting: synthesis and characterizeration of polymeric receptors for cholesterol", J. Am. Chem. Soc., 117(27), 7105-7111 (1995).*
Wulff et al., "Enzyme-analogue built polymers, 4. On the synthesis of polymers containing chiral cavities and their use for the resolution of racemates", Makromol. Chem. 178, 2799-2816 (1977).*
"International Application Serial No. PCT/EP2008/051729, International Search Report mailed Jun. 9, 2008", 5 pgs.
"International Application Serial No. PCT/EP2008/051729, Written Opinion mailed Jun. 9, 2008", 7 pgs.
Ekberg, B., et al., "Molecular Imprinting: A Technique for Producing Specific Separation Materials", *Trends in Biotech*, 7, (1989), 92-96.
Shea, K. J., et al., "Molecular Recognition on Synthetic Amorphous Surfaces. The Influence of Functional Group Positioning on the Effectivness of Molecular Recognition", *J. Am. Chem. Soc.*, 108(5), (1986), 1091-1093.
Whitcombe, M. J., et al., "A new method for the introduction of recognition site functionality into polymers prepared by molecular imprinting: synthesis and characterizeration of polymeric receptors for cholesterol", *J. Am. Chem. Soc.*, 117(27), (1995), 7105-7111.
Wulff, G., et al., "Enzyme-analogue built polymers, 4. On the synthesis of polymers containing chiral cavities and their use for the resolution of racemates", *Makromol. Chem.*, 178(10), (1977), 2799-2816.
"European Application Serial No. 08708948.8, Office Action mailed Mar. 2, 2012", 8 pgs.
Wulff, G., et al., "Enzyme-analogue-built polymers, 22. Influence of the nature of the crosslinking agent on the performance of imprinted polymers in recemic resolution", *Makromol. Chem.*, 188, (1987), 731-740.
Wulff, G., et al., "Enzyme-analogue-built polymers, 23. Influence of the structure of the binding sites on the selectivity for racemic resolution", *Makromol. Chem.*, 188, (1987), 741-748.
Wulff, G., "Enzyme-like Catalysis by Molecularly Imprinted Polymers", *Chemical Reviews*, 102(1), (2002), 1-27.
Wulff, G., et al., "Racemic Resolution of Free Sugars with Macroporous Polymers Prepared by Molecular Impriting. Selectivity Dependence on the Arrangement of Functional Groups versus Spatial Requirements", *The Journal of Organic Chemistry*, 56(1), (1991), 395-400.

* cited by examiner

*Primary Examiner* — Ling-Siu Choi
(74) *Attorney, Agent, or Firm* — Schwegman, Lundberg & Woessner, P.A.

(57) ABSTRACT

The present invention relates to molecularly imprinted polymers, methods for their preparation and use of said molecularly imprinted polymers in separation, chemical sensors, drug screening, catalysis and in regioselective and enantioselective synthesis.

12 Claims, 3 Drawing Sheets

Figure 1. Reversible esterification of a mannose derivative with vinylphenyl boronic acids
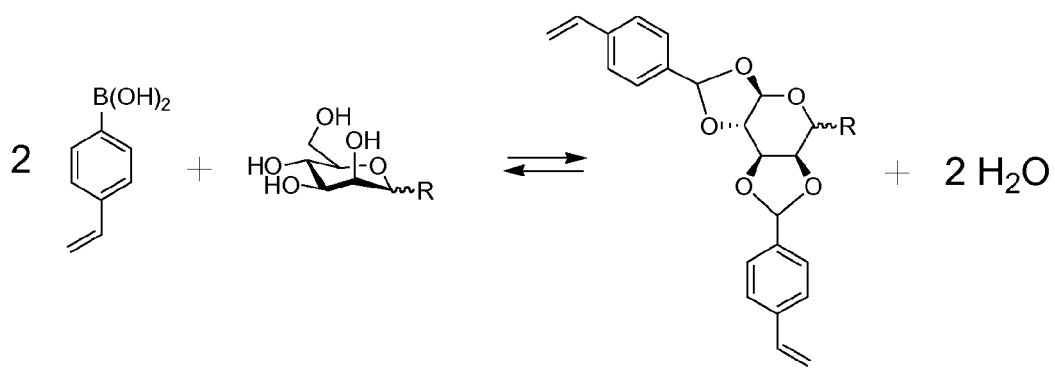
Figure 2. Schematic presentation of covalent imprinting using boronic acid monomers and monosaccharide templates.
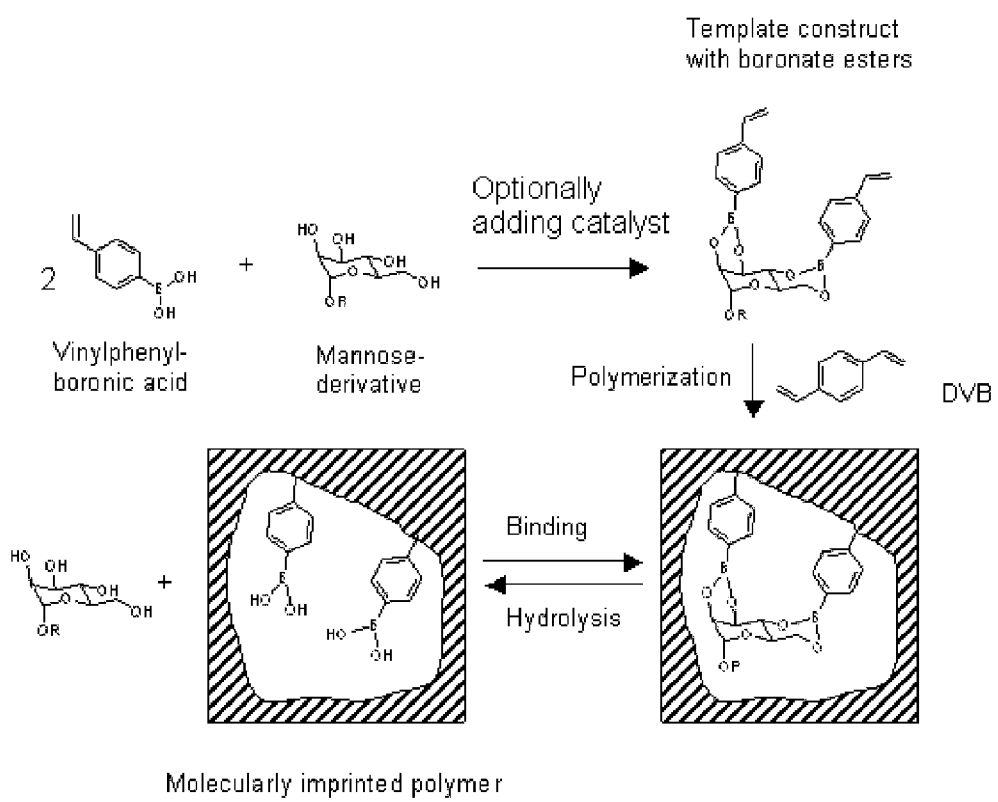

Figure 3. Chromatographic separation of two carbohydrates from example 1 (mobile phase: ethanol containing 0.25% ammonia)
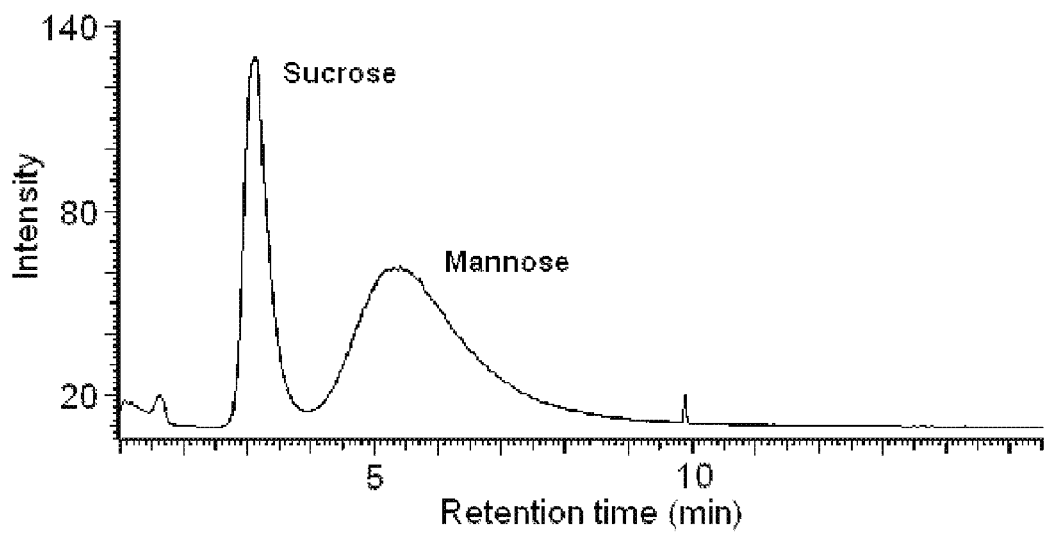
Figure 4. Chromatographic separation of two carbohydrates by a MIP in 100 % aqueous solvents from example 3 (mobile phase: 1% aqueous ammonia).
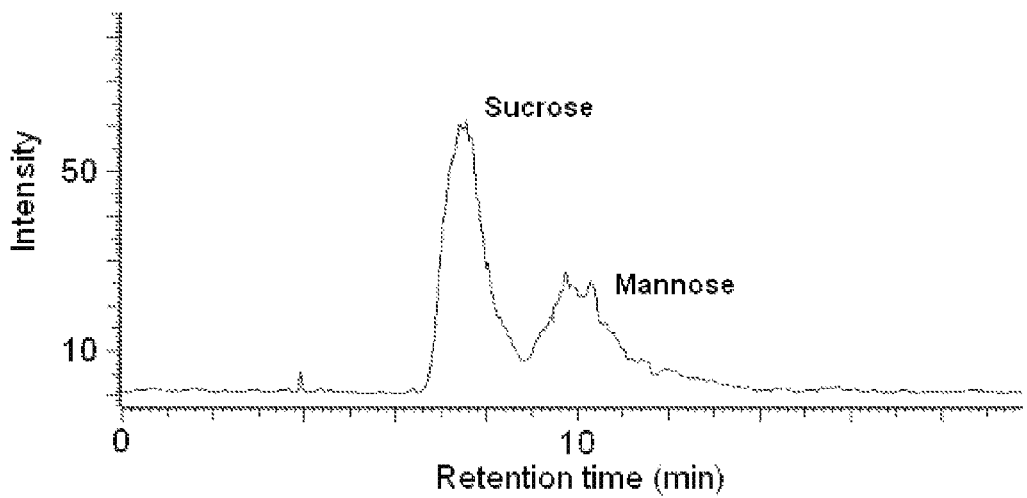

Figure 5. Overlayed chromatograms of L-lysine on L-lysine imprinted MIP and non-imprinted control polymer (NIP) from example 4.
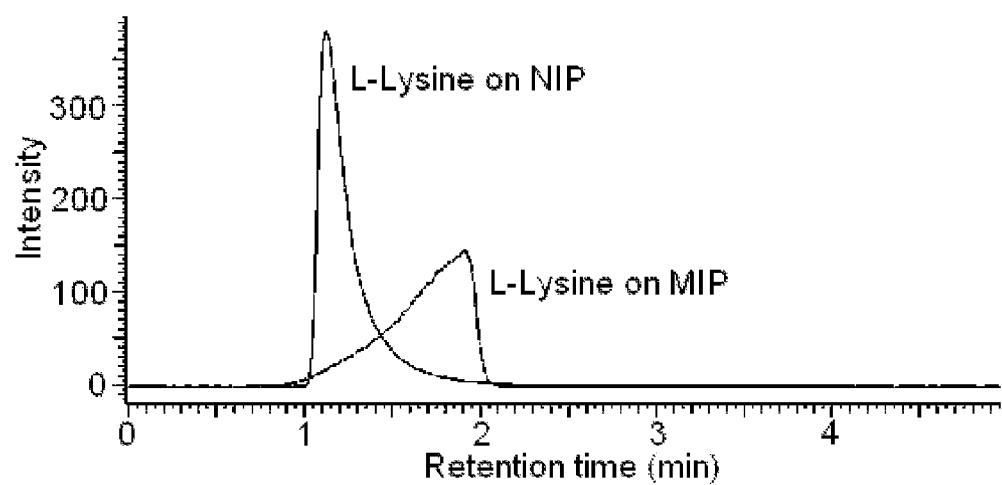

IMPRINTED POLYMERS

RELATED APPLICATIONS

This application is a nationalization under 35 U.S.C. 371 of PCT/SE2008/051729, filed Feb. 13, 2008 and published as WO 2008/107271 A1 on Sep. 12, 2008, which claimed priority under U.S.C. 119 to Sweden Application No. 0700546-5, filed Mar. 5, 2007, which applications and publication are incorporated herein by reference and made a part hereof.

TECHNICAL FIELD OF THE INVENTION

The present invention relates to molecularly imprinted polymers, methods for their preparation and use of said molecularly imprinted polymers in separation, chemical sensors, drug screening, catalysis and in regioselective and enantioselective synthesis.

BACKGROUND ART

In 1972, Wulff and Sarhan (Angew. Chem. 1972, 84, 364) introduced a method to produce polymer materials with a built-in specificity. Within these polymers, spatially defined cavities formed during the polymerization were responsible for the specificity. These polymers were prepared as follows: First pre-formed template-monomer complexes were prepared by chemical coupling of appropriate monomers to the desired templates by covalent bonds. The template-monomer complexes were then polymerized together with a cross-linking monomer in the presence of a porogenic solvent to obtain a porous polymer. An important feature of this method is that the covalent bonds between template and monomer are reversible so that the covalent template-polymer complex can be cleaved under conditions that preserve the polymer integrity, allowing release of the template and hence access to the cavities formed. Such polymers are now known as molecularly imprinted polymers and the preparation method described above is known as the covalent imprinting technique.

The majority of systems described were based on the pairing of vinyl-phenyl-boronic acid with diol-containing templates such as glyceric acid or simple monosaccharides or monosaccharide derivatives. For example, mannose derivatives were shown to undergo reversible esterification with vinyl-phenyl-boronic acids (FIG. 1) and several studies of this system were conducted, e.g. as described by Wulff et al. in Makromol. Chem. 178, 2799-2815 or J. Chromatogr. 1978, 167, 171-186.

Other reversible-covalent systems that were used in covalent imprinting involved monomers that could form Schiff bases (e.g. as disclosed by Wulff et al, React. Polym. 1984, 2, 167-174) and acetals or ketals (e.g. as disclosed by Shea and Dougherty, J. Am. Chem. Soc. 1986, 108, 1091-1093).

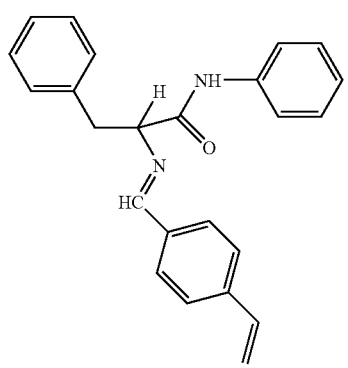

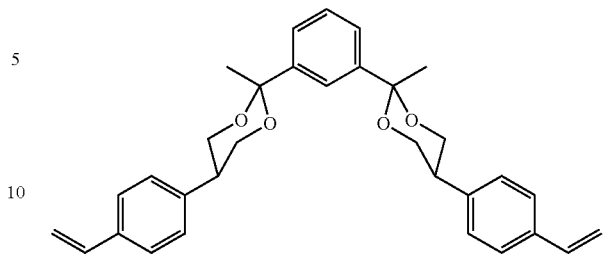

A further development appeared after the covalent imprinting approach had been described and was termed 'non-covalent imprinting'. According to this approach, monomers are allowed to interact non-covalently in solution with the template molecules e.g. through ionic interactions or hydrogen bonding. This method has obvious advantages over the covalent approach, e.g. the molecularly imprinted polymer is prepared in a one pot system, i.e. monomers, templates and initiator are mixed in a porogenic solvent followed by polymerisation. Furthermore a much higher number of monomers can be utilized for forming the template interaction. Today several hundred potential monomers are commercially available, providing an inherent flexibility, e.g. as disclosed by B. Sellergren, Molecularly Imprinted Polymer: Manmade mimics of antibodies and their applications in analytical chemistry, Elsevier Publishers, 2001. However, the inherent weakness of non-covalent bonds also gives rise to disadvantages, such as the low stoichiometry that is often achieved, i.e. low percentage of template molecules bound to monomer(s), leading to a low yield of binding sites. Non-covalently imprinted polymers generally have a lower capacity compared to covalently imprinted polymers. Furthermore, the non-covalent method often result in inhomogeneity of the binding sites and there is a need to optimize the type of porogenic solvent used for each imprinting recipe whereas covalent imprinting is much less sensitive to the influence of porogenic solvents present during the polymerization.

An intermediate synthetic route is disclosed by Whitcombe and et al. (J. Am. Chem. Soc. 1995, 117, 7105-7111), in which the template is first covalently linked to a polymerizable moiety and after polymerization and hydrolysis of bound template target compounds are able to rebind to the site via non-covalent interactions.

While covalent imprinting suffers from the drawbacks discussed above, it also has several advantages. For example, the capacity, i.e. number of binding sites per gram of MIP, of covalently prepared MIPs is often a factor of 10 higher compared to those prepared by non-covalent methods. The low capacity of traditionally prepared non-covalent MIPs is sometimes considered as a hindrance to their use in separation applications at the preparative or process scale. Despite these advantages, the preparation of MIPs by the covalent strategy is too costly and time consuming and laborious to be commercially viable. First, covalent MIP preparation entails often difficult synthetic steps to prepare the template-monomer covalent complex. Furthermore, we have observed that highly polar template molecules carrying charged or other polar groups may, even after linkage to the relevant monomer, exhibit complete insolubility in the non-polar solvents commonly used in molecular imprinting. Thus, conventional covalent imprinting excludes the use of many candidates, e.g. polyhydroxy compounds, naturally occurring polar compounds, hydrophilic pharmaceuticals, peptides and peptoids, oligosaccharides etc, as templates for MIP formation. For example, for the imprinting of oligosaccharides, where not all hydroxyl groups can undergo ester formation with vinylphenyl-boronic acids, the final template construct is often not soluble in organic solvents. A method that would allow such diverse molecular classes, previously excluded from traditional imprinting technologies, to be used as templates in a covalent imprinting approach and that would eliminate the need for the laborious synthetic steps involved in the preparation of covalently linked template-monomer complexes would be extremely valuable.

A recent publication (Mayes and Whitcombe, 2005) Advanced Drug Delivery Review, 2005, 57, 1742-1778) states the following: "The distinct disadvantages of all covalent strategies are the need for some level of synthetic chemistry to be carried out on the template before polymerization and a chemical treatment on the polymer to release template.", and "Today it (the non-covalent approach) is the predominant method used, because it offers much more flexibility in terms of the functionalities on a template that can be targeted. It also requires much less chemistry than the pre-synthesis of covalent adducts". Consequently, it is generally accepted by persons skilled in the art that covalent imprinting approaches require the pre-synthesis of adducts (template-monomer complexes) prior to polymerization.

Consequently, the possibility of being able to prepare a covalently imprinted molecularly polymer without the need for laborious and costly pre-synthesis would be of great value.

SUMMARY OF THE INVENTION

The present invention relates to a molecularly imprinted polymer, wherein the advantages of the simple preparation of non-covalently imprinted molecularly polymers are combined with the advantages of covalently imprinted polymers, said molecularly imprinted polymer is obtainable by
   a) providing at least one monomer and at least one template molecule in a solvent system, wherein said monomer and said template forms a covalent template-monomer complex by reversible self-assembly;
   b) optionally providing a cross-linking monomer;
   c) polymerizing said mixture;
   d) removing said at least one template molecule;
   e) optionally performing at least steps a)-c) in one reaction vessel without isolation of said template-monomer complex prior to polymerisation;
wherein said solvent system is selected from a solvent or a solvent mixture that enables the formation of said reversible self-assembly.

In one aspect the present invention relates to a molecularly imprinted polymer, obtained as above, and wherein the solvent system is an aqueous solvent system, or an aqueous solvent system that may contain organic solvent.

In one aspect the present invention relates to a molecularly imprinted polymer, obtainable as above, and wherein an agent promoting the formation of said reversible covalent bonds is present.

In one additional aspect the present invention relates to said molecularly imprinted polymer as defined above and wherein at least steps a)-c) are performed in one reaction vessel without isolation of said template-monomer complex prior to polymerisation.

In one aspect the present invention relates to the use of said molecularly imprinted polymer in separation, chemical sensors, drug screening, catalysis, and in regioselective or enantioselective synthesis.

Furthermore, the present invention relates to methods of preparing the molecularly imprinted polymer as described above.

SHORT DESCRIPTION OF THE FIGURES

FIG. 1 is an illustration of the formation of reversible covalent bonds.

FIG. 2 schematically illustrates a covalent imprinting process.

FIG. 3 illustrates chromatographic separation of two carbohydrates by the use of a molecularly imprinted polymer as prepared in Example 1.

FIG. 4 illustrates chromatographic separation of two carbohydrates in an aqueous mobile phase by the use of a molecularly imprinted polymer as prepared in Example 3.

FIG. 5 illustrates the imprinting effect of L-lysine by the use of a molecularly imprinted polymer as prepared in Example 4 and a non-imprinted polymer.

DETAILED DESCRIPTION OF THE PRESENT INVENTION

The present invention relates to a molecularly imprinted polymer, wherein the advantages of the simple preparation of non-covalently imprinted molecularly polymers are combined with the advantages of covalently imprinted polymers, said molecularly imprinted polymer is obtained as disclosed herein.

The present invention also relates to a novel route that combines the simple process of non-covalent imprinting with the advantages of covalent imprinting, such as the high capacities obtained through stoichiometric assemblies. Additionally, the present invention enables imprinting of hydrophilic templates that are currently excluded from standard imprinting protocols on solubility grounds. The present inventors have observed that the pre-formation of boronic acid esters with oligosaccharides may be cumbersome and the final adduct, due to potentially having a number of residual non-reacted hydroxyl or other polar/charged groups, is often insoluble in organic solvents that are commonly used in traditional molecular imprinting.

It is known in the art that sugars and similar compounds bind to boronic acids at basic pH values. The present inventors have used this fact and imprinted oligosaccharides in a self-assembly imprinting process, wherein vinyl-phenyl-boronic acid is used as a monomer (FIG. 2) and the solvent system is designed so that it allow the spontaneous formation of covalent bonds between the oligosaccharide and the vinylphenyl-boronic acid monomer. Such a solvent system can be an aqueous solvent system containing water and a water-miscible co-solvent such as methanol or N,N-dimethylformamide; or it may be an organic solvent such as chloroform, toluene; or a mixture of organic solvents. The solvent system may also include an agent that promotes the formation of covalent bonds between the template and the monomer. For the vinyl-phenylboronic acid monomer, ammonia and piperidine have been found to be useful. Preferred solvent systems are water/methanol/ammonia, water/N,N-dimethylformamide/ammonia and methanol/piperidine.

The supporting additives, preferably basic compounds, which e.g. can be selected from a nitrogen containing base such as ammonia or piperidine, have been shown to be useful. Surprisingly it was observed that firstly, the addition of the additive, which is present at rather high concentrations, did not inhibit or negatively influence the effectiveness of the imprinting procedure and secondly, the self-assembled covalent complexes being formed resulted in a highly effective MIP material. Thirdly, the novel imprinting technique of the present invention effectively produced molecularly imprinted polymers in aqueous (porogenic) solvents. In one embodiment according to the present invention such new MIP materials were able to separate certain oligosaccharide mixtures, resulting in separation factors that cannot be obtained with other conventional phase, currently used in carbohydrate separation. For example, the productivity number (mass of oligosaccharide mixture separated per unit mass of MIP per hour, typically kg/kg/hour) using MIPs of the present invention in place of commonly used resins may be increased by at least one order of magnitude and the inventors have observed factors of up to 25 times.

In one embodiment of the present invention, the imprinting of templates that can undergo Schiff-base formation with appropriate monomers may be carried out. For example, native amino acids are not soluble in organic solvents which are typically used in molecular imprinting.

In one embodiment according to the present invention, a carbonyl-containing monomer, such as acrolein or 3-vinylbenzaldehyde, or a ketone can be used to form a Schiff base with free amine of an amino acid, e.g. lysine, in an aqueous or non-aqueous solvent system and following addition of a cross-linker a molecularly imprinted polymer is formed.

The resulting aldehyde functionalities in the final polymer may not exhibit sufficiently fast kinetics or sufficient stability for storage. Consequently the aldehydes may be oxidized to carboxylic groups, accurately positioned from the molecular imprinting process, to display strong ionic interactions with a multitude of varying chiral and non-chiral targets that may fit into the sites.

In analogy with the above, the formation of oximes, ketals, acetals, hemiketals, hemiacetals, hemithioacetals or hemiaminals between the template and the monomer(s) can also be used for imprinting in aqueous or non-aqueous solvent systems.

A further advantage of the present invention is the flexibility conferred on the use of solvents and solvent mixtures. For example, in traditional non-covalent imprinting the majority of porogenic solvents are usually aprotic and of low dielectric constant. Widely used solvents are toluene, acetonitrile or chlorinated solvents, such as dichloromethane. The presence of water often has a destructive interference effect and is therefore a component to be eliminated under most circumstances. The present invention allows water to be used in the imprinting process to ensure the solubility of the polar template-monomer assemblies in preparation of a molecularly imprinted polymer according to the present invention. This allows for the use of hydrophilic templates which previously could not be used due to their low solubility in non-polar solvents. Such hydrophilic templates can be for example carbohydrates, amino acids, peptides and water-soluble drugs or drug-like molecules. For example, oligo-saccharides or carbohydrates may be imprinted with boronate monomers in engineered solvent systems (eg water containing methanol and ammonia, which promotes the formation of covalent bonds). Amino acids, peptides and other compounds that contain amino groups may be imprinted with monomer systems that utilize aldehyde monomers that form Schiff bases in water-free solvent systems (eg toluene or chlorinated solvents).

A further advantage of the invention is that covalently linked template-monomer complexes may be formed directly in the polymerization mixture, i.e. by self-assembly, so that the whole process can be carried out in a one pot system where no laborious pre-synthesis, work-up and purification of the template-monomer complex is required.

As used in the present invention the term "self-assembly" denotes a spontaneous assembly resulting in a covalently linked template-monomer complex, optionally in the prescence of a promoting agent, such as a basic compound e g selected from nitrogen-containing compounds, such as piperidine and ammonia, or alkali metal hydroxides, such as potassium hydroxide, sodium hydroxide and lithium hydroxide, or an acid, such as sulphuric acid and p-toluenesulphonic acid.

In the present invention the terms "covalently linked template-monomer" and "covalent template-monomer" are used interchangably.

As used in the present invention the term "monomer" means either or both of a functional monomer and/or a cross-linking monomer the latter of which may able to behave both as a functional monomer and a cross-linker.

The terms "additive", "promoting agent", "an agent promoting" and "catalyst" may be used interchangably within the present invention.

As used in the present invention the terms "basic compound", "basic" or "base" means a compound with Brönsted or Lewis basicity. As used in the present invention the term "one pot system" means that the template-monomer complex is obtained in one reaction vessel without isolation of said template-monomer complex prior to polymerisation.

In the present invention the terms "adduct" and "template-monomer complex" are used interchangeably.

Whenever the terms "solvent" is used it means a porogenic solvent.

The present invention is further illustrated by way of examples, which are to be considered as non-limiting examples.

EXAMPLES

Example 1

Aqueous Imprinting of a Saccharide with Vinylphenylboronic Acid under High pH Conditions Methyl-Mannoside (1 mmol) is dissolved in 5 ml of methanol containing 5% ammonia and 30% water. To this alkaline sugar solution, the monomer 4-vinylphenylboronic acid (2 mmol) and the cross-linker ethylene glycol dimethacrylate (20 mmol) are added along with an initiator (azobisdimethylvaleronitrile). In the absence of ammonia, the components are not soluble which indicates the occurrence of solubilisation through complex formation in the presence of ammonia. Polymerization is then initiated by heat and allowed to proceed over night. Grinding followed by sieving yields a MIP powder, which is washed and dried.

In chromatographic experiments, such a MIP displays a high selectivity towards the imprinted species, as illustrated in FIG. 3.

Example 2

Aqueous Imprinting of a Saccharide with Vinylphenylboronic Acid and with an Incorporated Basic Moiety Methyl-Mannoside (1 mmol) is dissolved in 5 ml of water containing 70% methanol. To this sugar solution, the monomer 4-vinylphenylboronic acid (2 mmol), the basic co-monomer 4-vinylbenzylamine (2 mmol) and the cross-linker ethylene glycol dimethacrylate (20 mmol) are added along with an initiator (azobisdimethylvaleronitrile). Polymerization is then initiated by heat and allowed to proceed overnight. Grinding followed by sieving yields a MIP powder, which is then washed and dried.

In chromatographic experiments, such a MIP also displays a high selectivity towards the imprinted species at lower pH values.

Example 3

Aqueous Imprinting of a Saccharide with Vinylphenylboronic Acid and with an Incorporated Hydrophilic Moiety Methyl-Mannoside (1 mmol) is dissolved in 5 ml of methanol containing 5% ammonia and 30% water. To this basic sugar solution, the monomer 4-vinylphenylboronic acid (2 mmol), the hydrophilic co-cross-linker 1,4-bismethacryloylpiperazine (5 mmol) and the cross-linker ethylene glycol dimethacrylate (15 mmol) are added along with an initiator (azobisdimethyl-valeronitrile). Polymerization is then initiated by heat and allowed to proceed overnight. Grinding followed by sieving yields a MIP powder which is then washed and dried.

In chromatographic experiments, such a MIP displays a high selectivity towards the imprinted species in purely water-based mobile phases, as illustrated in FIG. 4.

Example 4

Aqueous Imprinting of an Amine-containing Template with an Aldehyde Monomer

The amino acid L-lysine (1 mmol) and potassium hydroxide (1 mmol) are dissolved in 4.2 ml of methanol containing 20% of water so that a solution of potassium L-lysinate, having a free amino group, is obtained. To this solution, the aldehyde monomer (acrolein or vinylbenzaldehyde, 2 mmol) and the cross-linker ethyleneglycol dimethacrylate (15 mmol) are added along with an initiator (azobisdimethylvaleronitrile). Polymerization is then initiated by heat, UV or chemically and allowed to proceed until completion. Grinding followed by sieving yields a MIP powder which is washed and dried.

The binding capacity of this MIP was found to be 0.13 mmol/g. This is considerably higher than what is typical for non-covalently imprinted polymers, see Yilmaz et al, Anal. Commun., 1999, 36, 167-170.

Example 5

Oxidiation and Use in Chromatography

This oxidation step is done to transform the aldehyde functionality of the MIP from example 4 to carboxylic acid functionalites.

MIP powder from example 4 (2.0 g) was suspended in 20 ml of dimethyl sulfoxide (20 mL) and a solution of sodium chlorite (5 mmol) and sodium dihydrogen phosphate (1 mmol) in 20 ml of water was added. The mixture was stirred overnight and the polymer was then filtered off and washed with water and methanol. The same procedure was repeated with a non-imprinted control polymer (NIP) that had been prepared in the absence of L-lysine and potassium hydroxide.

In chromatographic experiments, L-lysine was found to have longer retention time on the MIP than on the NIP as illustrated in FIG. 5. This demonstrates successful imprinting leading to selective binding of lysine.

Example 6

Aqueous Imprinting of an Aldehyde-containing Template with an Amine Monomer

The template molecule glutaraldehyde (1 mmol) is dissolved in 5 ml of water containing dimethyl sulfoxide. To this solution, the monomer 4-vinylaniline (2 mmol) and a cross-linker (ethyleneglycol dimethacrylate, 15 mmol) are added along with an initiator (azobisdimethylvaleronitrile). Polymerization is then initiated by heat, UV or chemically and allowed to proceed until completion. Grinding followed by sieving yields a MIP powder which is washed and dried. Other polymerisable aromatic or aliphatic amines, e.g. 4-vinylbenzylamine may also be used.

Example 7

Aqueous Imprinting of a Ketone-containing Template with an Amine Monomer

The aqueous imprinting of a ketone-containing template was performed similar to example 6, with the exception that 1,4-diacetylbenzene was used as the template molecule.

Example 8

Aqueous Imprinting of an Aldehyde or Ketone-containing Template with a Hydroxylamine Monomer Example 8 was performed similar to example 6 or 7, with the exception that O-(4-vinylbenzyl) hydroxylamine was used as the monomer. Other polymerisable hydroxylamines may also be used.

Example 9

Imprinting of an Aldehyde-containing Template with a Monomer that can Form an Acetal with the Template The template molecule terephthalaldehyde (1 mmol) is dissolved in 5 ml toluene. To this solution, the monomer 2-(4-vinylphenyl)-1,3-propanediol (2 mmol) is added together with a cross-linker (ethyleneglycol dimethacrylate, 15 mmol) and an initiator (azobisdimethylvaleronitrile). Optionally, an acidic catalyst may also be added. Polymerization is then initiated by heat, UV or chemically and allowed to proceed until completion. Grinding followed by sieving yields a MIP powder which is then washed and dried. Additionally, other polymerizable 1,2- or 1,3-diols such as glycerol monoacrylate or glycerol monomethacrylate may also be used.

Example 10

Imprinting of a Ketone-containing Template with a Monomer that can Form an Acetal with the Template Example 10 was done similarly to example 9 but 1,4-diacetylbenzene was used as the template molecule.

Example 11

Imprinting of an Aldehyde or Ketone-containing Template with a Monomer that can Form a Thioacetal with the Template Example 11 was done similarly to example 9 or 10, but 2-(4-vinylphenyl)-1,3-propanedithiol was used as the monomer. Other polymerisable 1,2- or 1,3-dithiols may also be used.

Example 12

Imprinting of an Alcohol-containing Template with a Monomer than can Form a Hemiacetal with the Template The template molecule beta-estradiol (1 mmol) is dissolved in 5 ml toluene. To this solution, the monomer 4'-acrylamido-2,2,2-trifluoro-acetophenone (2 mmol) is added together with a cross-linker (ethyleneglycol dimethacrylate, 15 mmol) and an initiator (azobisdimethylvaleronitrile). Optionally, an acidic or basic catalyst may also be added. Polymerization is then initiated by heat, UV or chemically and allowed to proceed until completion. Grinding followed by sieving yields a MIP powder which is then washed and dried. Other polymerisable ketones or aldehydes may also be used.

Example 13

Imprinting of an Amine-containing Template with a Monomer than can Form a Hemiaminal with the Template The imprinting of an amine-containing template was performed similar to example 12, but with piperazine as the template molecule.

Any of the examples above may be produced by any polymerization process that is amenable to large-scale production, such as normal or inverse suspension polymerization, film formation, composite formation, grafting onto solid supports or any other desired format. For example, the monomer mixture may be produced in a suspension mode with varying continuous phases, it could be emulsified in an appropriate continuous phase, produced by membrane emulsification, prepared as a composite in a porous support bead or network or membrane or coated onto a fiber or fibrous matrix.

A person skilled in the art may find applications areas of such imprinted materials in diverse fields, such as general separations, diagnostic elements, sensors, pharmaceutical devices including controlled release materials, biomimetic or engineered surfaces on medical devices, textiles, filters and other materials.

The invention claimed is:

1. A method of producing a molecularly imprinted polymer comprising
   a) providing at least one monomer and at least one template molecule in a solvent system, wherein said monomer and said template forms a covalent template-monomer complex by reversible self-assembly, wherein an agent promoting the formation of said reversible self-assembly is present;
   b) optionally providing a cross-linking monomer;
   c) polymerizing said mixture;
   d) removing said at least one template molecule;
   e) optionally performing at least steps a)-c) in one reaction vessel without isolation of said template-monomer complex prior to polymerisation;
      wherein said solvent system is selected from a solvent or a solvent mixture that enables the formation of said reversible self-assembly.

2. The method according to claim 1, wherein said solvent system is an aqueous solvent system.

3. The method according to claim 2, wherein said aqueous solvent system contains organic solvent.

4. The method according to claim 1, wherein said agent is a basic compound.

5. The method according to claim 1, wherein said basic compound is selected from nitrogen-containing compounds, or alkali metal hydroxides.

6. The method according to claim 1, wherein at least steps a)-c) is performed in one reaction vessel without isolation of said template-monomer complex prior to polymerisation.

7. The method according to claim 1, wherein the template is selected from hydrophilic molecules having low solubility in organic solvents.

8. The method according to claim 1, wherein the template is selected from the group consisting of drug-like templates, chiral templates, carbohydrates, amino acids, peptides and oligonucleotides.

9. The method according to claim 1, wherein the polymerization process is selected from the group consisting of solution polymerization, bulk polymerization, precipitation polymerization, emulsion polymerization, suspension polymerization, composite formation and grafting process, membrane emulsification, and swelling techniques.

10. The method according to claim 1, wherein said monomer is selected from monomers comprising at least one functional group selected from the group consisting of an aldehyde, a boronic acid, an amine, a hydroxylamine, a diol, a hemiacetal, a thiol, a dithiol and a ketone.

11. The method according to claim 5, wherein the nitrogen-containing compound is piperidine or ammonia.

12. The method according to claim 5, wherein the alkali metal hydroxides is potassium hydroxide, sodium hydroxide or lithium hydroxide.

* * * * *